United States Patent [19]

Gluckman

[11] Patent Number: 4,840,174

[45] Date of Patent: Jun. 20, 1989

[54] METHOD OF LASER TREATMENT OF CANCERIZATION OF THE ORAL CAVITY

[75] Inventor: Jack L. Gluckman, Cincinnati, Ohio

[73] Assignee: University of Cincinnati, Cincinnati, Ohio

[21] Appl. No.: 136,556

[22] Filed: Dec. 22, 1987

Related U.S. Application Data

[62] Division of Ser. No. 879,401, Jun. 27, 1986, Pat. No. 4,736,745.

[51] Int. Cl.$^4$ .............................................. A61B 17/36
[52] U.S. Cl. ................................................. 128/303.1
[58] Field of Search ..................................... 128/12–16, 128/20, 23, 303.1, 395–398, 664, 665; 362/223, 224, 259, 804, 84; 433/29, 31, 93, 140; 424/101

[56] References Cited

U.S. PATENT DOCUMENTS

| | | |
|---|---|---|
| 1,266,659 | 5/1918 | Brannan . |
| 2,800,896 | 7/1957 | Thum . |
| 3,769,963 | 11/1973 | Goldman et al. . |
| 3,916,880 | 11/1975 | Schroer . |
| 4,290,433 | 9/1981 | Alfano . |
| 4,323,056 | 4/1982 | Borrelli et al. . |
| 4,336,809 | 6/1982 | Clark . |
| 4,385,344 | 5/1983 | Gonser . |
| 4,395,397 | 7/1983 | Shapiro . |
| 4,592,344 | 6/1986 | Scheer . |

FOREIGN PATENT DOCUMENTS

| | | |
|---|---|---|
| 674647 | 10/1930 | France . |
| 507078 | 2/1954 | Italy . |
| 2125986 | 3/1984 | United Kingdom . |
| 2126717 | 8/1984 | United Kingdom . |

OTHER PUBLICATIONS

Jack Gluckman, "Photodynamic Therapy-Viable Alternative to Conventional Therapy for Early Lesion of the Upper Aerodigestive Tract", 5/5/85.

Primary Examiner—Max Hindenburg
Attorney, Agent, or Firm—Wood, Herron & Evans

[57] ABSTRACT

Cancer of the oral cavity is treated by sensitizing malignant and premalignant tissue and non-selectively irradiating the entire oral cavity with a destructive laser. The strength or intensity of the light is adjusted so that non-sensitized tissue is not damaged. A special holder adapted to permit irradiation of the entire oral cavity from two fiber optic diffusers is also disclosed.

11 Claims, 1 Drawing Sheet

METHOD OF LASER TREATMENT OF CANCERIZATION OF THE ORAL CAVITY

BACKGROUND

Cancer effects virtually every part of the human anatomy. Each area of cancerization is unique and requires unique treatment. The present invention involves treatment of cancer localized in the oral cavity. Because of the difficulty in determining the extent of premalignant and malignant change, cancerization of the oral cavity is extremely difficult to manage. Current methods of treating this problem include excision, cryosurgery, $CO_2$ laser ablation, and selective destruction of premalignant as well as early malignant tumors by photodynamic therapy.

Any type of selective excision of condemned mucosa of the oral cavity presents inherent difficulties. It is extremely difficult to clinically differentiate malignant, premalignant, and benign mucosa because frequently the entire oral cavity mucosa appear to be condemned.

Photodynamic therapy, PDT, has been used in various treatments of cancers. Photodynamic therapy is a relatively new therapeutic modality which uses a photosensitizing drug such as hematoporphyrin derivative (HPD) or its purified form dihematoporphyrin ether (DHE) which selectively localizes in tumors and on activation by exposure to light results in cell necrosis.

The first described use of such a photosensitizer in a biological system occurred at the turn of the century when the lethal affect of acridine dye on paramecium incubated and exposed to light was reported. Numerous other substances have subsequently been used as photosensitizers, for example tetracycline, berberine sulphate, acridine orange, fluoresceine as well as various porphyrins. Porphyrins are particularly preferred since they are selectively taken up by tumor cells.

HPD and DHE appear to fill most of the criteria for a satisfactory photosensitizer for use in diagnosis and treatment of malignant diseases in humans. The treatment using HPD and DHE is disclosed for example in Clark U.S. Pat. No. 4,336,809 and U.K Patent Application No. 2,125,986. The methods disclosed in these references suffer from the same disadvantage of the prior methods of treatment of cancer of the oral cavity in that they are used to destroy or remove specific tissue. This requires identification and selection of the diseased tissue which is difficult if not impossible.

SUMMARY OF THE INVENTION

The present invention is premised upon the realization that cancer of the oral cavity can be treated using photodynamic therapy wherein the cancerous tissue of the aerodigestive tract is photosensitized and subsequently the entire oral cavity is non-selectively irradiated by an effective amount of laser generated light to destroy the sensitized tissue but without causing substantial damage to any other of the nonsensitized, i.e., non cancerous tissue.

Further, this invention is premised on the realization that by positioning fiber optic laser generators or diffusers parallel to the axis of the left and right molars, in the oral cavity, one can irradiate substantially the entire oral cavity. The present invention is further premised on the realization that a unique holder can be adapted to facilitate lasing of substantially the entire oral cavity.

The present invention provides for mounting in a holder two fiber optic laser generators also called diffusers within the oral cavity and parallel to the molars, the holder held in position by the teeth of the patient. This permits total non selective irradiation of the oral cavity and permits shielding of any localized areas where the radiation is excessive such as on the lateral portions of the tongue and the buccal mucosa.

The present invention will be further appreciated in light of the following detailed description and drawings in which:

DETAILED DESCRIPTION

According to the present invention, cancerization of the oral cavity is treated by sensitizing cancerous tissue using a sensitizing agent and subsequently non-selectively irradiating substantially the entire oral cavity with an appropriate lasing device.

The sensitizing agent is generally applied intravascularly. The preferred sensitizing agents are hematoporphyrin derivative and dihematoporphyrin ether. Specifically a patient is injected with hematoporphyrin derivative 3.0 mg/kg body weight or dihematoporphyrin ether at 2.0 mg/kg body weight preferably 72 hours prior to therapy Substantially the entire oral cavity is then non-selectively illuminated with 20 to 30 Joules/cm$^2$ of laser light. Preferably 30 J/cm$^2$ is an adequate dose in the oral cavity. The normal mucosa tolerate up to 50 J/cm$^2$.

According to the method of the present invention, the laser device generally comprises a pair of fiber optic bundles connected to a laser.

Various lasing devices are currently used in photodynamic therapy. For example, Clark U.S. Pat. No. 4,336,809 discusses the use of a Xenon laser. Shapiro U.S. Pat. No. 4,395,397 discusses the argon laser, neodyium YAG, Krypton ion or dye lasers. Two preferred lasers are the argon dye laser or the gold vapor laser. The general requirement for a suitable laser is that it provides sufficient energy at a wavelength at which the sensitizing agent is effective. This will of course vary depending on the sensitizing agent employed. Generally HDP and DHE sensitize cancerous tissue to 630 nM wavelength light.

Figure 1:
FIG. 1 is a diagramatic depiction of a laser system for use in the present invention.
Figure 2:
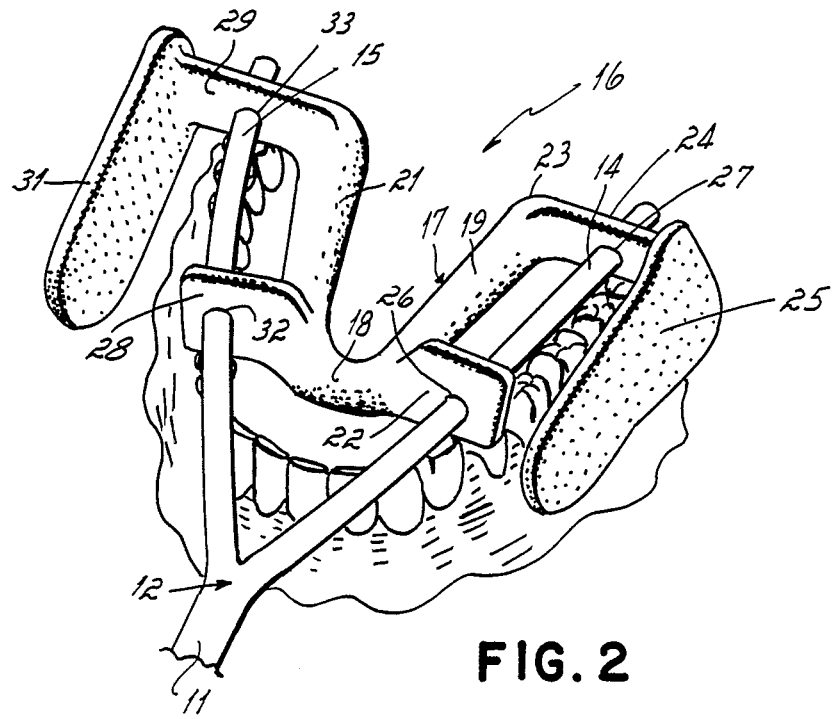
FIG. 2 is an overhead perspective view of the apparatus for use in the present invention resting on the lower jaw of an individual.
Figure 3:
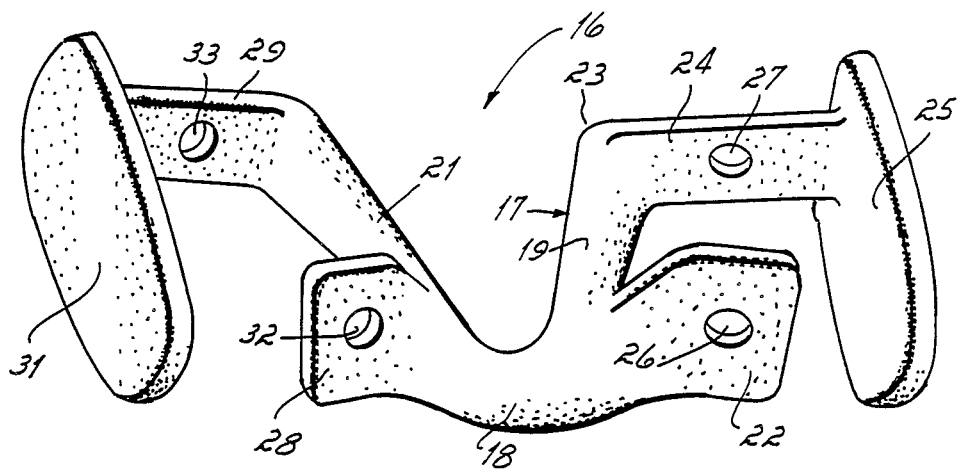
FIG. 3 is a perspective view of an apparatus for use in the present invention.

The lasers used should transmit light through a fiber optic bundle. As shown diagrammatically in FIG. 1, there is a laser light generator 10 emitting light to fiber optic bundle 11. The fiber optic bundle is connected to a couple 12 which divides the transmitted light between two cylindrical fiber optic diffusers 14 and 15. These act to emit light in all directions from the fiber optic bundle. Various diffusers are discussed in Clark U.S. Pat. No. 4,336,809.

The fiber optic diffusers 14 and 15 are aligned above and parallel to the left and right lateral teeth line for appropriate non selective irradiation of the entire oral cavity.

In order to accomplish this, a special holder 16 is used. Holder 16 includes a C-shaped interior frame 17. The C-shaped frame 17 includes an anterior central portion 18 and left and right side frame members 19 and 21 respectively. The anterior portion of the left side frame member includes a outwardly extended tab 22. The posterior portion 23 of left side member 19 includes a tangentially extending arm 24. Arm 24 includes a left prong 25 which extends parallel to the left side member 19 and is adapted to force the cheek of an individual outwardly.

Left tab 22 and left arm 24 define first and second apertures 26 and 27 respectively which are adapted to support the first fiber optic diffuser 14. The apertures 26 and 27 are aligned so that when the holder 16 is positioned in the mouth of an individual, the tab 22 and side member 24 will rest on the left lateral tooth line with the apertures aligned directly above the teeth, i.e., parallel to an axis from the first premolar to the second premolar on the left portion of the oral cavity.

The right side frame member 21 also includes a lateral tab 28 extended from the anterior portion of the right side frame member 21. Also extending from frame member 21 is a right tangentially extended arm 29 which includes or supports a right prong 31 which extends parallel to the right side frame member 21. Tab 28 and arm 29 include aligned apertures 32 and 33 respectively which are adapted to support second fiber optic diffuser 15. Again, when the holder 16 is positioned in a patient's mouth, the apertures 32 and 33 are designed to rest along the right side tooth line supporting diffuser 15 between the upper and lower right molar teeth, i.e., parallel to an axis from a first premolar to a second premolar on the right portion or side of the oral cavity.

As designed, this holder 16 supports left and a right side fiber optic diffuser 14 and 15 positioned within the oral cavity of an individual. The tabs 22 and 28 and arms 29 and 31 rest on the teeth and are grasped by the teeth of the patient. Prongs 25 and 31 then act to push the left and right cheek portion of the mouth outwardly exposing the ridge.

The fiber optic diffuser 14 and 15 are preferably 2 cm cylindrical tipped quartz optical fibers coupled to a helium neon laser. The holder 12 is preferably formed from a material which is transparent to the light emitted by the laser and therefore does not interfere with irradiation of any portion of the oral cavity. Clear dental acrylic is suitable for this purpose.

Table I presents the relative effective illumination at various areas of the oral cavity when a device such as the holder 16 is employed. This shows both the effective illumination at 30 J/cm$^2$ and compensated illumination at 50 J/cm$^2$. In the event that the effective dosage to the buccal mucosa reaches 50 J/cm$^2$, basically all areas of the mouth would be provided with an effective dosage. The lateral surface of the tongue would be exposed to excessively high amounts of energy which would cause lingual edema. Therefore an effective shield would be required. A tongue shield (not shown) can be used for lateral portions of the tongue to avoid exposure to the radiation. This can also be accomplished by opacifying the arms 19 and 21 of the holder 16. Incorporation of an appropriate filler such as clay, talc, titanium dioxide or other materials which would reduce the transparency of the arm about 50-75% would provide an adequate shield for the lateral portion of the tongue.

TABLE I

| Anatomic Location | Effective illumination at 30 J/cm$^2$ (J/cm$^2$) | Compensated illumination at 30 J/cm$^2$ (J/cm$^2$) |
| --- | --- | --- |
| Buccal Mucosa | 30 | 50 |
| Gingivo-Buccal Sulcus (Inf.) | 10.9 | 18.2 |
| Gingivo-Buccal Sulcus (Sup.) | 12.8 | 21.4 |
| Palate | 16.57 | 27.5 |
| Floor of Mouth | 16.75 | 27.9 |
| Lat. Surface of Tongue | 72 | 120 |

The only area which showed relatively inadequate treatment was the small area between the alveolar ridge and the lips. This, however, is not important since this area is rarely a site for malignant change. If necessary, this area can be treated separately or a modification can be made to allow a small cylindrical diffuser to be held in this area.

It is also possible to irradiate the oral cavity without the use of two diffusers. Although less preferred, a single diffuser can be placed in apertures 26 and 27 and the left side of the oral cavity irradiated. The diffuser is then removed from apertures 26 and 27 and positioned in apertures 32 and 33 to irradiate the right side of the oral cavity. This effectively irradiates the entire oral cavity and requires only one diffuser.

Accordingly, holder 16 permits substantially the entire oral cavity to be non-selectively irradiated. By selectively choosing the radiation dosage and effectively sensitizing cancerous tissue, one can employ this device to treat cancer of the oral cavity tract without actively distinguishing malignant and premalignant tissue.

Thus having described my invention, I claim:

1. A method of treating field cancerization of the oral cavity comprising sensitizing premalignant and malignant tissue to a destructive light;
   non-selectively irradiating substantially all of the oral cavity with said destructive light by emitting said destructive light through at least one optical diffuser positioned within said oral cavity said destructive light being of an intensity and duration effective to damage said premalignant and malignant tissue.

2. The method claimed in claim 1 wherein substantially all of said oral cavity is radiated at one time from at least one light source.

3. The method claimed in claim 1 wherein said oral cavity is irradiated by light emitted from a laser through said optical diffuser.

4. The method claimed in claim 3 wherein said light is emitted through a plurality of fiber optic diffusers.

5. The method claimed in claim 4 wherein said light is emitted from two fiber optic diffusers.

6. The method claimed in claim 5 comprising positioning a first fiber optic diffuser parallel to an axis from a first premolar to a second premolar on the left portion of the oral cavity and a second diffuser on an axis from a first premolar to a second molar on the right portion of said oral cavity.

7. The method claimed in claim 5 wherein said two fiber optic diffusers are held in position by a holder transparent to said laser light.

8. The method claimed in claim 4 wherein said light has a wavelength of about 630 nM.

9. The method claimed in claim 4 wherein said oral cavity is radiated with light providing less than about 50 Joules/cm$^2$.

10. The method claimed in claim 9 wherein said oral cavity is radiated with light providing about 20-30 Joules/cm$^2$.

11. The method claimed in claim 1 further comprising blocking at least a portion of said oral cavity from said destructive light to prevent heat destruction of said portion of said oral cavity.

* * * * *